United States Patent
Takahashi

(10) Patent No.: US 11,317,885 B2
(45) Date of Patent: May 3, 2022

(54) RADIOGRAPHIC IMAGE PROCESSING DEVICE, METHOD OF OPERATING RADIOGRAPHIC IMAGE PROCESSING DEVICE, AND RADIOGRAPHIC IMAGE PROCESSING PROGRAM

(71) Applicant: FUJIFILM Corporation, Tokyo (JP)

(72) Inventor: Tomoyuki Takahashi, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 160 days.

(21) Appl. No.: 16/831,713

(22) Filed: Mar. 26, 2020

(65) Prior Publication Data

US 2020/0305829 A1  Oct. 1, 2020

(30) Foreign Application Priority Data

Mar. 29, 2019 (JP) .............................. JP2019-066182

(51) Int. Cl.
| | |
|---|---|
| *G06K 9/00* | (2022.01) |
| *G01V 5/00* | (2006.01) |
| *A61B 6/00* | (2006.01) |
| *G06T 7/00* | (2017.01) |

(52) U.S. Cl.
CPC ............ *A61B 6/5282* (2013.01); *A61B 6/465* (2013.01); *A61B 6/54* (2013.01); *G06T 7/0012* (2013.01)

(58) Field of Classification Search
USPC ........ 382/100, 103, 106–108, 128–132, 172, 382/173, 181, 199, 216, 224, 254, 382/274–277, 286–291, 305, 318; 250/395, 267
See application file for complete search history.

(56) References Cited

U.S. PATENT DOCUMENTS

| | | | |
|---|---|---|---|
| 9,704,241 B2* | 7/2017 | Imai | ........................ G06V 10/44 |
| 9,842,395 B2* | 12/2017 | Imai | ........................ G06V 10/44 |
| 10,342,503 B2 | 7/2019 | Kobayashi et al. | |
| 2014/0361192 A1* | 12/2014 | Imai | ........................ G01T 1/16 |
| | | | 250/336.1 |

(Continued)

FOREIGN PATENT DOCUMENTS

| | | |
|---|---|---|
| JP | 2015051081 | 3/2015 |
| JP | 6006193 | 10/2016 |

(Continued)

OTHER PUBLICATIONS

Office Action of Japan Counterpart Application, with English translation thereof, dated Feb. 1, 2022, pp. 1-8.

*Primary Examiner* — Seyed H Azarian
(74) *Attorney, Agent, or Firm* — JCIPRNET

(57) ABSTRACT

A region detection image is obtained by the detection of a subject region of a radiographic image in which radiation is transmitted through a subject and reaches a radiation detection unit and a direct radiation region of the radiographic image in which the radiation directly reaches the radiation detection unit without being transmitted through the subject. A scattered radiation image about scattered radiation components is obtained on the basis of the region detection image and scattered-radiation-spread information about the spread of scattered radiation. A radiographic image from which the scattered radiation components have been removed is obtained by the subtraction of the scattered radiation image from the radiographic image.

11 Claims, 6 Drawing Sheets

(56) References Cited

U.S. PATENT DOCUMENTS

2015/0379711 A1* 12/2015 Imai .................... A61B 6/5282
                                                          382/132
2016/0235384 A1*  8/2016 Enomoto ............. A61B 6/4291

FOREIGN PATENT DOCUMENTS

| JP | 6006454    | 10/2016 |
| JP | 2016198176 | 12/2016 |
| JP | 2017185080 | 10/2017 |
| JP | 2017189379 | 10/2017 |

* cited by examiner

RADIOGRAPHIC IMAGE PROCESSING DEVICE, METHOD OF OPERATING RADIOGRAPHIC IMAGE PROCESSING DEVICE, AND RADIOGRAPHIC IMAGE PROCESSING PROGRAM

CROSS-REFERENCE TO RELATED APPLICATIONS

This application claims priority under 35 U.S.C § 119(a) to Japanese Patent Application No. 2019-066182 filed on 29 Mar. 2019. The above application is hereby expressly incorporated by reference, in its entirety, into the present application.

BACKGROUND OF THE INVENTION

1. Field of the Invention

The present invention relates to a radiographic image processing device, a method of operating the radiographic image processing device, and a radiographic image processing program that process a radiographic image obtained from the imaging of a subject irradiated with radiation.

2. Description of the Related Art

A diagnosis, which uses a radiographic image obtained in a case where a subject irradiated with radiation is imaged by a radiation detection unit, is made in a medical field. Scattered radiation causing the contrast of a subject to deteriorate is included in radiation that is transmitted through the subject and reaches the radiation detection unit, in addition to primary radiation. Accordingly, the components of scattered radiation are removed from the radiographic image to prevent the deterioration of contrast.

In, for example, JP6006193B (corresponding to U.S. Pat. No. 9,704,241B2), the characteristics of a virtual grid corresponding to the type of a grid to be assumed to be used to remove scattered radiation are acquired and scattered radiation of a radiographic image is removed on the basis of the characteristics of the virtual grid. Further, in JP6006454B, it is possible to apply the same scattered radiation removal effect as a scattered radiation-removal grid, which is actually used, to a radiographic image that is obtained in a case where a subject is imaged using a grid, by removing scattered radiation from a radiographic image, which is obtained in a case where a grid is used, on the basis of the characteristics of a virtual grid different from the used grid.

SUMMARY OF THE INVENTION

The scattered radiation of a direct radiation region based on radiation, which directly reaches a radiation detection unit without being transmitted through a subject, is included as the components of scattered radiation, in addition to the scattered radiation of a subject region based on radiation transmitted through a subject. The scattered radiation of the direct radiation region is generated from a top board provided between the subject and the radiation detection unit. The scattered radiation of the direct radiation region also causes the contrast of the radiographic image to deteriorate. The removal and the like of the scattered radiation of the direct radiation region are not described and suggested in both JP6006193B and JP6006454B.

An object of the invention is to provide a radiographic image processing device, a method of operating the radiographic image processing device, and a radiographic image processing program that can estimate scattered radiation of a direct radiation region based on radiation directly reaching a radiation detection unit without being transmitted through a subject and can remove the scattered radiation.

A radiographic image processing device according to an aspect of the invention comprises an image acquisition unit that acquires a radiographic image obtained in a case where a subject irradiated with radiation is imaged by a radiation detection unit, a region detection unit that obtains a region detection image by detecting a subject region of the radiographic image in which the radiation is transmitted through the subject and reaches the radiation detection unit and a direct radiation region of the radiographic image in which the radiation directly reaches the radiation detection unit without being transmitted through the subject, a scattered radiation image-acquisition unit that obtains a scattered radiation image about a scattered radiation component on a basis of the region detection image and scattered-radiation-spread information about spread of scattered radiation, and a scattered radiation component-removal unit that obtains a radiographic image from which the scattered radiation component has been removed by subtracting the scattered radiation image from the radiographic image.

It is preferable that the region detection unit detects a region of the radiographic image in which a pixel value is smaller than a threshold value for a region as the subject region, and detects a region of the radiographic image in which a pixel value is equal to or larger than the threshold value for a region as the direct radiation region. It is preferable that the radiographic image processing device further comprises a direct radiation region-pixel value-calculation unit that obtains an unsaturated scattered radiation pixel value corresponding to a dose of radiation for imaging, which is the dose of the radiation with which the subject is irradiated, with reference to an unsaturated-scattered-radiation-pixel-value relationship representing a relationship between the dose of the radiation and the unsaturated scattered radiation pixel value which is an unsaturated pixel value obtained in consideration of an influence of the scattered radiation without saturation of the pixel value; and a pixel value replacement unit that replaces a pixel value of the direct radiation region of the scattered radiation image with the unsaturated scattered radiation pixel value, and the scattered radiation component-removal unit subtracts the scattered radiation image, of which the pixel value has been replaced with the unsaturated scattered radiation pixel value, from the radiographic image.

It is preferable that the unsaturated-scattered-radiation-pixel-value relationship is predetermined for each imaging condition in a table for the direct radiation region and the direct radiation region-pixel value-calculation unit uses any unsaturated-scattered-radiation-pixel-value relationship corresponding to the imaging condition at the time of imaging of the subject or uses a combination of a plurality of unsaturated-scattered-radiation-pixel-value relationships satisfying the imaging condition at the time of imaging of the subject, with reference to the table for the direct radiation region.

It is preferable that the radiographic image processing device further comprises a boundary position adjustment unit that adjusts a position of a boundary between the subject region and the direct radiation region by a specific width, and the scattered radiation image-acquisition unit obtains the scattered radiation image on a basis of the scattered radiation image in which the position of the boundary has been adjusted and the scattered-radiation-spread information about the spread of the scattered radiation. It is preferable that the position of the boundary is adjusted in a case where a pixel value of the direct radiation region exceeds a threshold value for a pixel value or a case where a dose of the radiation exceeds a threshold value for a dose of radiation.

It is preferable that the specific width is determined on a basis of at least one of a portion of the subject, a method of imaging the subject, a dose of the radiation, or imaging menu information. It is preferable that the specific width is determined on a basis of a value of a pixel positioned near the position of the boundary in the radiographic image.

It is preferable that the scattered-radiation-spread information is predetermined for each imaging condition in a table for scattered-radiation-spread information and the scattered radiation image-acquisition unit uses any scattered-radiation-spread information corresponding to the imaging condition at the time of imaging of the subject or uses a combination of a plurality of pieces of scattered-radiation-spread information satisfying the imaging condition at the time of imaging of the subject, with reference to the table for scattered-radiation-spread information.

It is preferable that the radiation is transmitted through the subject and a top board on which the subject is placed and is incident on the radiation detection unit, and the scattered-radiation-spread information is a function of determining two-dimensional spread of the scattered radiation of the radiation incident on any point on the top board.

A method of operating a radiographic image processing device according to another aspect of the invention comprises a step of causing an image acquisition unit to acquire a radiographic image obtained in a case where a subject irradiated with radiation is imaged by a radiation detection unit; a step of causing a region detection unit to obtain a region detection image by detecting a subject region of the radiographic image in which the radiation is transmitted through the subject and reaches the radiation detection unit and a direct radiation region of the radiographic image in which the radiation directly reaches the radiation detection unit without being transmitted through the subject; a step of causing a scattered radiation image-acquisition unit to obtain a scattered radiation image about a scattered radiation component on a basis of the region detection image and scattered-radiation-spread information about spread of scattered radiation; and a step of causing a scattered radiation component-removal unit to obtain a radiographic image from which the scattered radiation component has been removed by subtracting the scattered radiation image from the radiographic image.

A radiographic image processing program according to still another aspect of the invention causes a computer to perform image acquisition processing for causing an image acquisition unit to acquire a radiographic image obtained in a case where a subject irradiated with radiation is imaged by a radiation detection unit; region detection processing for causing a region detection unit to obtain a region detection image by detecting a subject region of the radiographic image in which the radiation is transmitted through the subject and reaches the radiation detection unit and a direct radiation region of the radiographic image in which the radiation directly reaches the radiation detection unit without being transmitted through the subject; scattered radiation image-acquisition processing for causing a scattered radiation image-acquisition unit to obtain a scattered radiation image about a scattered radiation component on a basis of the region detection image and scattered-radiation-spread information about spread of scattered radiation; and scattered radiation component-removal processing for causing a scattered radiation component-removal unit to obtain a radiographic image from which the scattered radiation component has been removed by subtracting the scattered radiation image from the radiographic image.

According to the invention, it is possible to estimate scattered radiation of a direct radiation region based on radiation directly reaching a radiation detection unit without being transmitted through a subject and to remove the scattered radiation.

DESCRIPTION OF THE PREFERRED EMBODIMENTS

Figure 1:
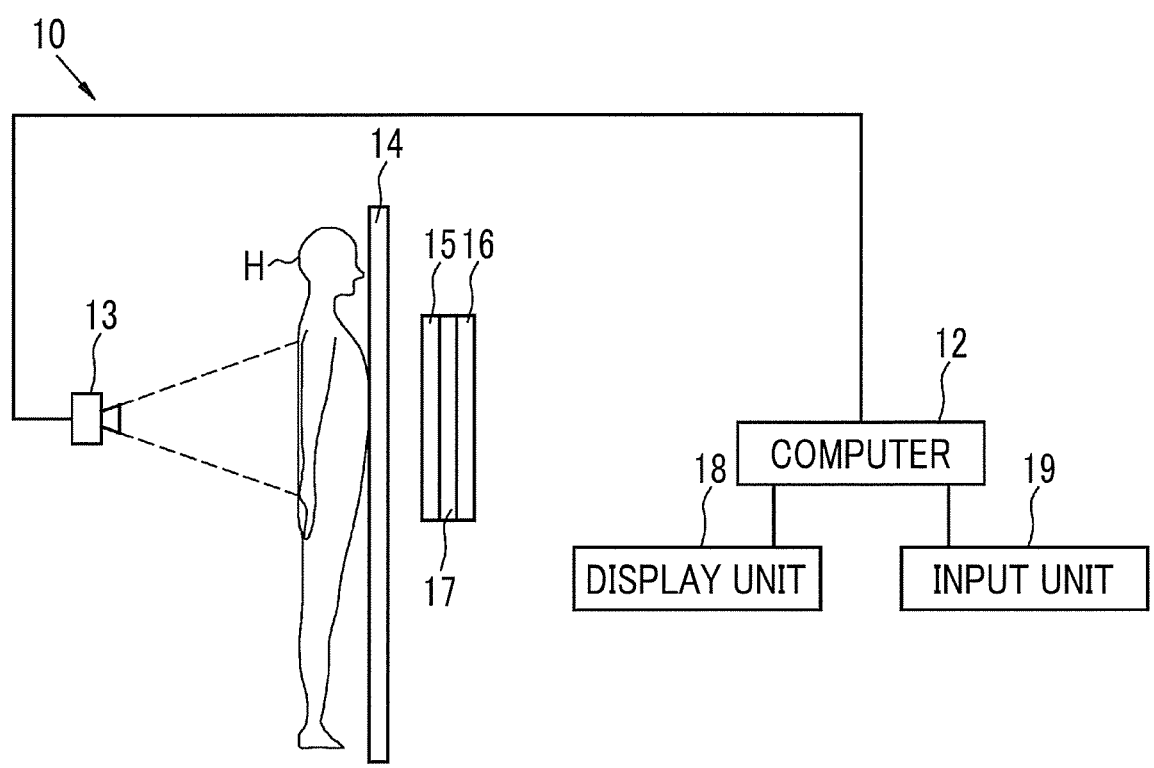
FIG. 1 is a schematic diagram of a radiographic imaging system.

As shown in FIG. 1, a radiographic imaging system comprises an imaging device 10 and a computer 12 and acquires two radiographic images having different energy distributions. In a case where the imaging device 10 receives radiation (for example, X-ray), which is emitted from a radiation source 13 and is transmitted through a subject H, through a top board 14 by a first radiation detector 15 and a second radiation detector 16, each of the first and second radiation detectors 15 and 16 converts the radiation into energy and receives the energy (one-shot energy subtraction). The top board 14, the first radiation detector 15, a radiation energy conversion filter 17 formed of a copper plate or the like, and the second radiation detector 16 are arranged in this order from the side close to the radiation source 13 and the radiation source 13 is driven at the time of imaging. The first and second radiation detectors 15 and 16 and the radiation energy conversion filter 17 are in close contact with each other. Further, a unit including the first and second radiation detectors 15 and 16 corresponds to a "radiation detection unit" of the invention.

Accordingly, a first radiographic image G1 of the subject H formed using low-energy radiation including so-called soft radiation is obtained in the first radiation detector 15. Further, a second radiographic image G2 of the subject H formed using high-energy radiation excluding soft radiation is obtained in the second radiation detector 16. The first and second radiographic images G1 and G2 are input to the computer 12. The computer 12 performs arithmetic processing (differential processing) and the like on the basis of the first and second radiographic images G1 and G2, so that a radiographic image in which soft parts, bone parts, and the like included in the subject H are emphasized is obtained. In a case where a scattered radiation-removal grid for removing scattered radiation components of radiation transmitted through the subject H is used at the time of imaging of the subject H in this embodiment, primary radiation components of the radiation transmitted through the subject H are included in the first and second radiographic images G1 and G2. On the other hand, in a case where the scattered radiation-removal grid is not used at the time of imaging of the subject H, primary radiation components and scattered radiation are included in the first and second radiographic images G1 and G2.

A so-called direct radiation detector that can repeatedly record and read out a radiographic image and generates electric charges by being directly irradiated with radiation may be used as each of the first and second radiation detectors 15 and 16. Alternatively, an indirect radiation detector that converts radiation into visible light and then converts the visible light into electric charge signals may be used as each of the first and second radiation detectors 15 and 16. It is preferable that a so-called optical reading method of reading out radiographic image signals by turning on and off a thin film transistor (TFT) switch is used as a method of reading out radiographic image signals.

A display unit 18 and an input unit 19 are connected to the computer 12. The display unit 18 is formed of a cathode ray tube (CRT) display, a liquid crystal display, or the like, and displays radiographic images acquired from imaging, and the like. The input unit 19 is formed of a keyboard, a mouse, a touch panel, or the like.

A radiographic image processing program is installed on the computer 12. The computer 12 may be a workstation or a personal computer that is directly operated by an operator, and may be a server computer that is connected to the workstation or the personal computer through a network. A subject information acquisition program is distributed in a state where the subject information acquisition program is recorded in a recording medium, such as a digital versatile disc (DVD) or a compact disc read only memory (CD-ROM); and is installed on the computer 12 from the recording medium. Alternatively, the subject information acquisition program is stored in the storage of a server computer, which is connected to a network, or a network storage in a state where a user can have access to the subject information acquisition program from the outside, and is downloaded and installed on the computer 12 on demand.

Figure 2:
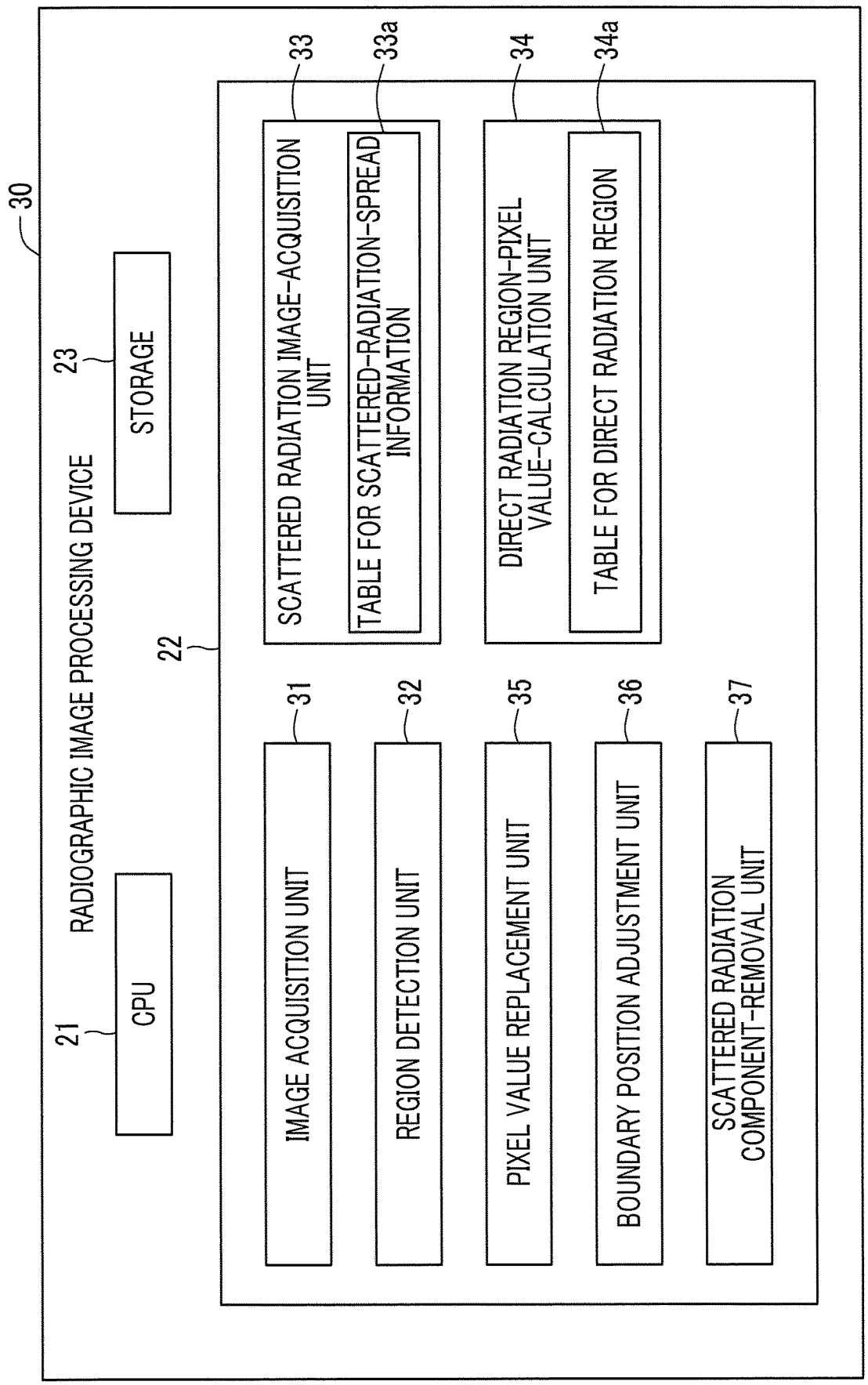
FIG. 2 is a block diagram showing the functions of a radiographic image processing device.

FIG. 2 shows the schematic configuration of a radiographic image processing device 30 that is realized by the installation of the radiographic image processing program on the computer 12. The radiographic image processing device 30 comprises a central processing unit (CPU) 21, a memory 22, and a storage 23. The storage 23 is formed of a storage device, such as a hard disk or a solid state drive (SSD), and various kinds of information that includes a program for driving the respective parts of the imaging device 10 and an acquisition program are stored in the storage 23. Further, radiographic images acquired from imaging are also stored in the storage 23.

The programs stored in the storage 23 and the like are temporarily stored in the memory 22 to cause the CPU 21 to perform various kinds of processing. As processing to be performed by the CPU 21, the subject information acquisition program prescribes: image acquisition processing for acquiring a radiographic image by causing the imaging device 10 to perform imaging; region detection processing for obtaining a region detection image by detecting a subject region of the radiographic image in which radiation is transmitted through the subject and reaches the radiation detection unit and a direct radiation region of the radiographic image in which radiation directly reaches the radiation detection unit without being transmitted through the subject; scattered radiation image-acquisition processing for obtaining a scattered radiation image about scattered radiation components on the basis of the region detection image and scattered-radiation-spread information about the spread of scattered radiation; and scattered radiation component-removal processing for obtaining a radiographic image from which scattered radiation components have been removed by subtracting the scattered radiation image from the radiographic image.

The CPU 21 is adapted to implement the functions of the respective parts by the radiographic image processing program in this embodiment. However, a programmable logic device (PLD) that is a processor of which the circuit configuration can be changed after the manufacture, such as a field programmable gate array (FPGA), can be used as a general-purpose processor functioning as various processing units by executing software, in addition to the CPU 21. Further, the processing of the respective parts may be performed by a dedicated electrical circuit that is a processor having circuit configuration designed exclusively to perform specific processing, such as an application specific integrated circuit (ASIC), and the like.

One processing unit may be formed of one of these various processors, or may be formed of a combination of two or more same kind or different kinds of processors (for example, a combination of a plurality of FPGAs, a combination of a CPU and an FPGA, or the like). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor implementing the functions of the entire system, which includes a plurality of processing units, by one integrated circuit (IC) chip is used as typified by System On Chip (SoC) or the like. In this way, various processing units are formed using one or more of the above-mentioned various processors as hardware structures.

In addition, the hardware structures of these various processors are more specifically electrical circuitry where circuit elements, such as semiconductor elements, are combined.

The radiographic image processing device 30 comprises an image acquisition unit 31, a region detection unit 32, a scattered radiation image-acquisition unit 33, a direct radiation region-pixel value-calculation unit 34, a pixel value replacement unit 35, a boundary position adjustment unit 36, and a scattered radiation component-removal unit 37.

The image acquisition unit 31 acquires the first and second radiographic images G1 and G2 that are detected by the first and second radiation detectors 15 and 16. In this embodiment, the chest and the abdomen of the subject H are imaged in this order and the first and second radiographic images G1 and G2 of the chest and the abdomen are acquired. The first and second radiographic images G1 and G2 are subjected to energy subtraction processing and the like, so that radiographic images in which soft parts, bone parts, and the like included in the subject are emphasized are obtained. The radiographic images are subjected to region detection processing and the like, and are used for the display of the display unit 18. The first and second radiographic images may be subjected to the region detection processing and the like without being subjected to the energy subtraction processing and the like. The first and second radiographic images G1 and G2 may be acquired from an external device separate from the radiographic image processing device 30, and may be stored in the storage 23. In this case, the image acquisition unit 31 reads out the first and second radiographic images G1 and G2 from the storage 23 for the processing of the first and second radiographic images G1 and G2 stored in the storage 23.

In a case where the first and second radiographic images are acquired by the image acquisition unit 31, an imaging condition is set. The imaging condition includes at least any one of the dose of radiation for imaging, a tube voltage, the thickness of the top board 14, source image receptor distances (SIDs) that are distances between the radiation source 13 and the surfaces of the first and second radiation detectors 15 and 16, a source object distance (SOD) that is a distance between the radiation source 13 and the surface of the subject H, the type of the scattered radiation-removal grid, the type of the filter, or whether or not the scattered radiation-removal grid is present. It is preferable that the imaging condition is set by an operator's input from the input unit 19. The set imaging condition is stored in the storage 23.

Figure 3:
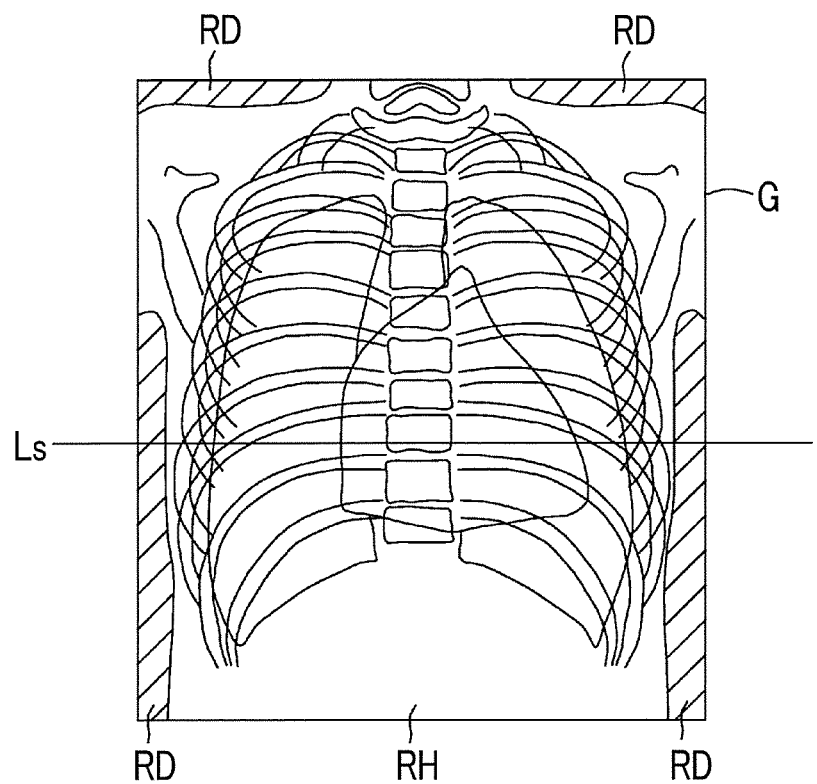
FIG. 3 is an image diagram showing a radiographic image.
Figure 4:
FIG. 4 is a diagram illustrating the region detection image of a specific line portion.

The region detection unit 32 obtains a region detection image by detecting a subject region of the radiographic image G in which radiation is transmitted through the subject H and reaches the first and second radiation detectors 15 and 16 and a direct radiation region of the radiographic image G in which radiation is transmitted through only the top board 14 without being transmitted through the subject H and directly reaches the first and second radiation detectors 15 and 16. Specifically, as shown in FIG. 3, the region detection unit 32 detects a region of the radiographic image G in which a pixel value is smaller than a threshold value for a region as a subject region RH, and detects a region of the radiographic image G in which a pixel value is equal to or larger than the threshold value for a region as a direct radiation region RD. For example, in a case where the region detection image is a binary image of which the subject region RH corresponds to "0" and the direct radiation region corresponds to "1", a distribution shown in FIG. 4 is obtained at a specific line Ls of the radiographic image G. The regions may be detected by artificial intelligence (AI) processing without using the threshold value for a region.

Since a threshold value for a region is determined for each imaging condition, it is preferable that a threshold value for a region corresponding to an imaging condition at the time of imaging of the subject H is used. Further, any one of the first radiographic image G1 or the second radiographic image G2 may be subjected to the region detection processing.

The scattered radiation image-acquisition unit 33 obtains a scattered radiation image about scattered radiation components on the basis of the region detection image and scattered-radiation-spread information about the spread of scattered radiation. The scattered radiation component-removal unit 37 obtains a radiographic image from which the scattered radiation components have been removed by subtracting the scattered radiation image from the radiographic image G. The radiographic image from which the scattered radiation components have been removed is displayed on the display unit 18.

Figure 5:
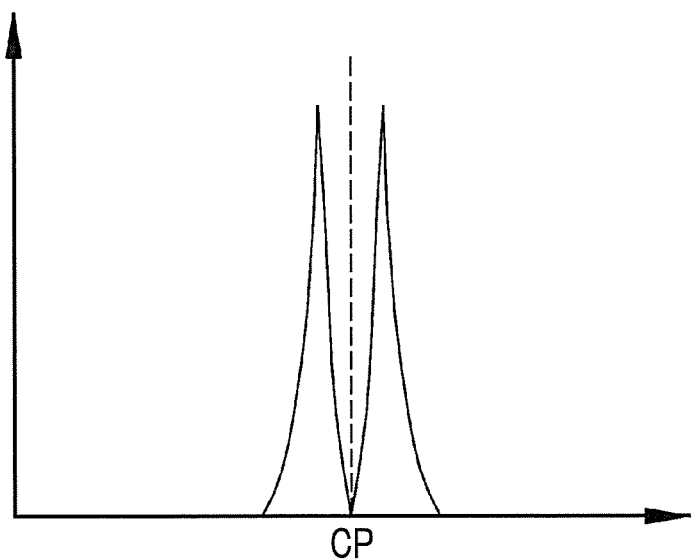
FIG. 5 is a graph showing a point spread function (PSF).

For example, a point spread function (PSF) that is a function determining the two-dimensional spread of scattered radiation of radiation incident on any point (incident point) on the top board 14 is used as the scattered-radiation-spread information used by the scattered radiation image-acquisition unit 33. In the PSF shown in FIG. 5, a central portion CP corresponding to the incident point of radiation is a primary radiation component and corresponds to "0". The PSF has peaks near the central portion CP, and is reduced as being away from the each peak. Since a PSF is determined for each imaging condition, it is preferable that a PSF corresponding to an imaging condition at the time of imaging of the subject H is used.

Scattered-radiation-spread information is predetermined for each imaging condition in a table 33a for scattered-radiation-spread information. The scattered radiation image-acquisition unit 33 uses any scattered-radiation-spread information corresponding to an imaging condition at the time of imaging of the subject H or uses a combination of a plurality of pieces of scattered-radiation-spread information satisfying an imaging condition at the time of imaging of the subject H, with reference to the table 33a for scattered-radiation-spread information. Further, it is preferable that the scattered-radiation-spread information is calculated using information about images taken according to a specific procedure. Furthermore, it is preferable that the scattered-radiation-spread information is generated on the basis of parameters. Moreover, it is preferable that the scattered-radiation-spread information is obtained by an input of information calculated in advance.

Then, a scattered radiation image including scattered radiation components is obtained in the scattered radiation image-acquisition unit 33 by an arithmetic operation based on Equation (1) that convolves the region detection image and the PSF.

$$\text{scattered radiation image} = \text{region detection image} * \text{PSF (here, * denotes a convolution operator)} \quad \text{Equation (1)}$$

The pixel value of the direct radiation region of the radiographic image G may be used, just as it is, as the pixel value of the scattered radiation component of the direct radiation region of the scattered radiation image, but the pixel value of the direct radiation region of the radiographic image is often saturated (often exceeds pixel values in which the imaging sensors of the first and second radiation detectors 15 and 16 can receive light). For this reason, it is preferable that an unsaturated scattered radiation pixel value, which is an unsaturated pixel value obtained in consideration of the influence of scattered radiation without the saturation of the pixel value, is theoretically calculated as the pixel value of the direct radiation region of the scattered radiation image and this theoretically calculated unsaturated scattered radiation pixel value is replaced as the pixel value of the direct radiation region of the scattered radiation image.

Figure 6:
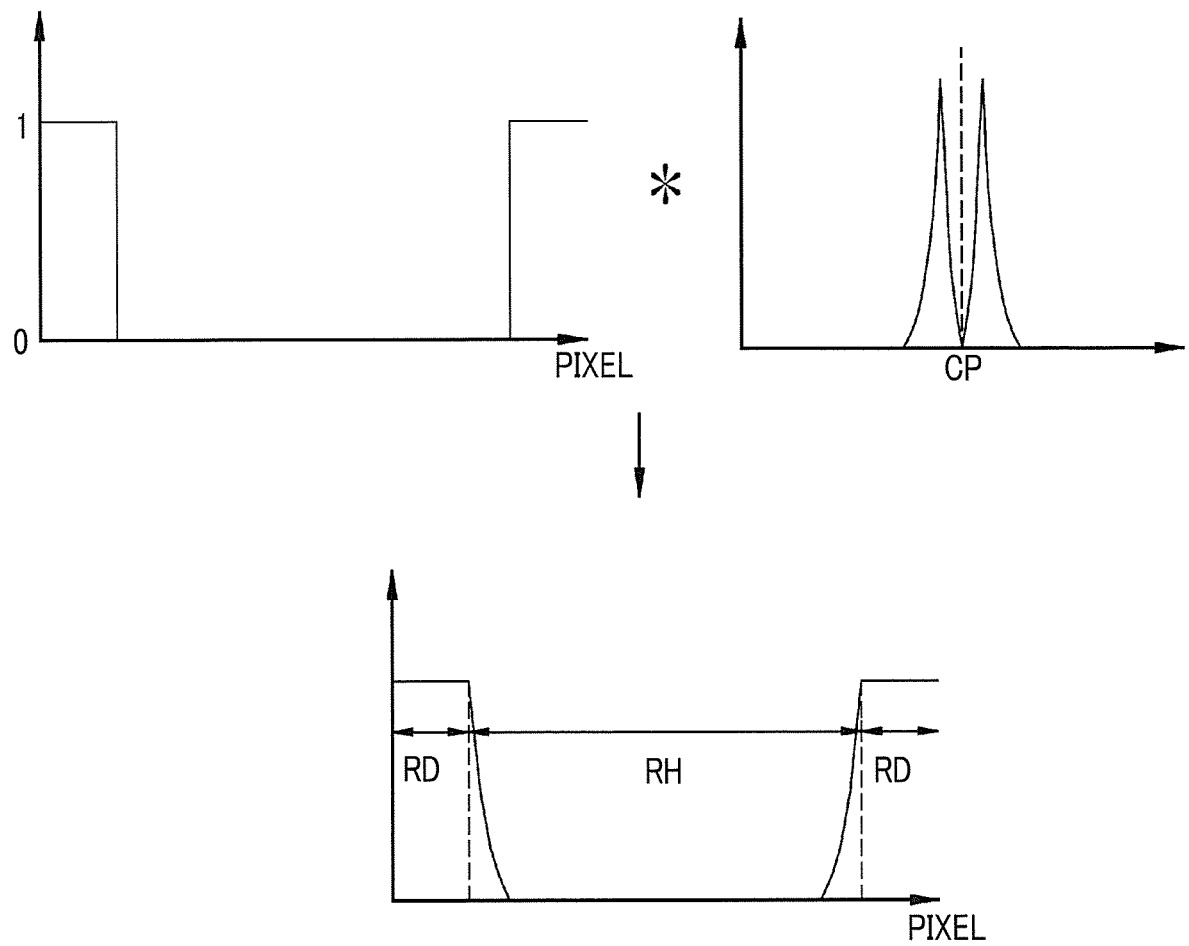
FIG. 6 is a diagram illustrating the scattered radiation image of a specific line portion that is obtained from the region detection image and PSF.

The direct radiation region-pixel value-calculation unit 34 calculates an unsaturated scattered radiation pixel value corresponding to the dose of radiation for imaging with reference to an unsaturated-scattered-radiation-pixel-value relationship representing a relationship between the dose of radiation and the unsaturated scattered radiation pixel value that is an unsaturated pixel value obtained in consideration of the influence of scattered radiation without the saturation of the pixel value. Then, the pixel value replacement unit 35 replaces the pixel value of the direct radiation region with the unsaturated scattered radiation pixel value. Specifically, as shown in FIG. 6, the pixel value replacement unit 35 replaces the pixel value of the direct radiation region RD of a scattered radiation image, which is obtained by an arithmetic operation based on Equation (1), with the unsaturated scattered radiation pixel value that is obtained by the direct radiation region-pixel value-calculation unit 34.

An unsaturated-scattered-radiation-pixel-value relationship is predetermined for each imaging condition in a table 34a for a direct radiation region. The direct radiation region-pixel value-calculation unit 34 uses any unsaturated-scattered-radiation-pixel-value relationship corresponding to an imaging condition at the time of imaging of the subject H or uses a combination of a plurality of unsaturated-scattered-radiation-pixel-value relationships satisfying an imaging condition at the time of imaging of the subject H, with reference to the table 34a for a direct radiation region. Further, it is preferable that the unsaturated scattered radiation pixel value is calculated on the basis of, for example, Equation (2).

unsaturated scattered radiation pixel value=(unsaturated pixel value obtained in a case where pixel value is not saturated)×(the content ratio of scattered radiation of direct radiation region)  Equation (2)

The region detection unit 32 distinguishes a subject region from a direct radiation region by using a threshold value for a region as described above, but there is a case where a region in which radiation is transmitted through a soft part region of a subject close to the skin is also included in the direct radiation region detected using a threshold value for a region. If a scattered radiation image is subtracted from a radiographic image G in a case where it is regarded that scattered radiation is emitted from even the soft part region, scattered radiation components are excessively removed. For this reason, the position of a boundary between the subject region and the direct radiation region is adapted to be capable of being adjusted by a specific width so that a scattered radiation image is obtained on the basis of the region detection image and the scattered-radiation-spread information after the adjustment of the position of the boundary.

The boundary position adjustment unit 36 adjusts the position of a boundary between the subject region and the direct radiation region by a specific width. It is preferable that the position of the boundary is adjusted in a case where the pixel value of the direct radiation region exceeds a threshold value for a pixel value or a case where the dose of radiation exceeds a threshold value for a dose of radiation. Further, it is preferable that the specific width is determined on the basis of at least one of a portion of the subject, a method of imaging the subject, the dose of radiation, or imaging menu information. Here, the imaging menu information is information about imaging conditions that can be set by a user. The imaging menu information is displayed on the display unit 18, and a user operates the input unit 19 to set any one of the imaging conditions displayed in the imaging menu information. Further, it is preferable that the specific width is determined on the basis of the values of pixels positioned near the position of the boundary in the radiographic image.

Figure 7:
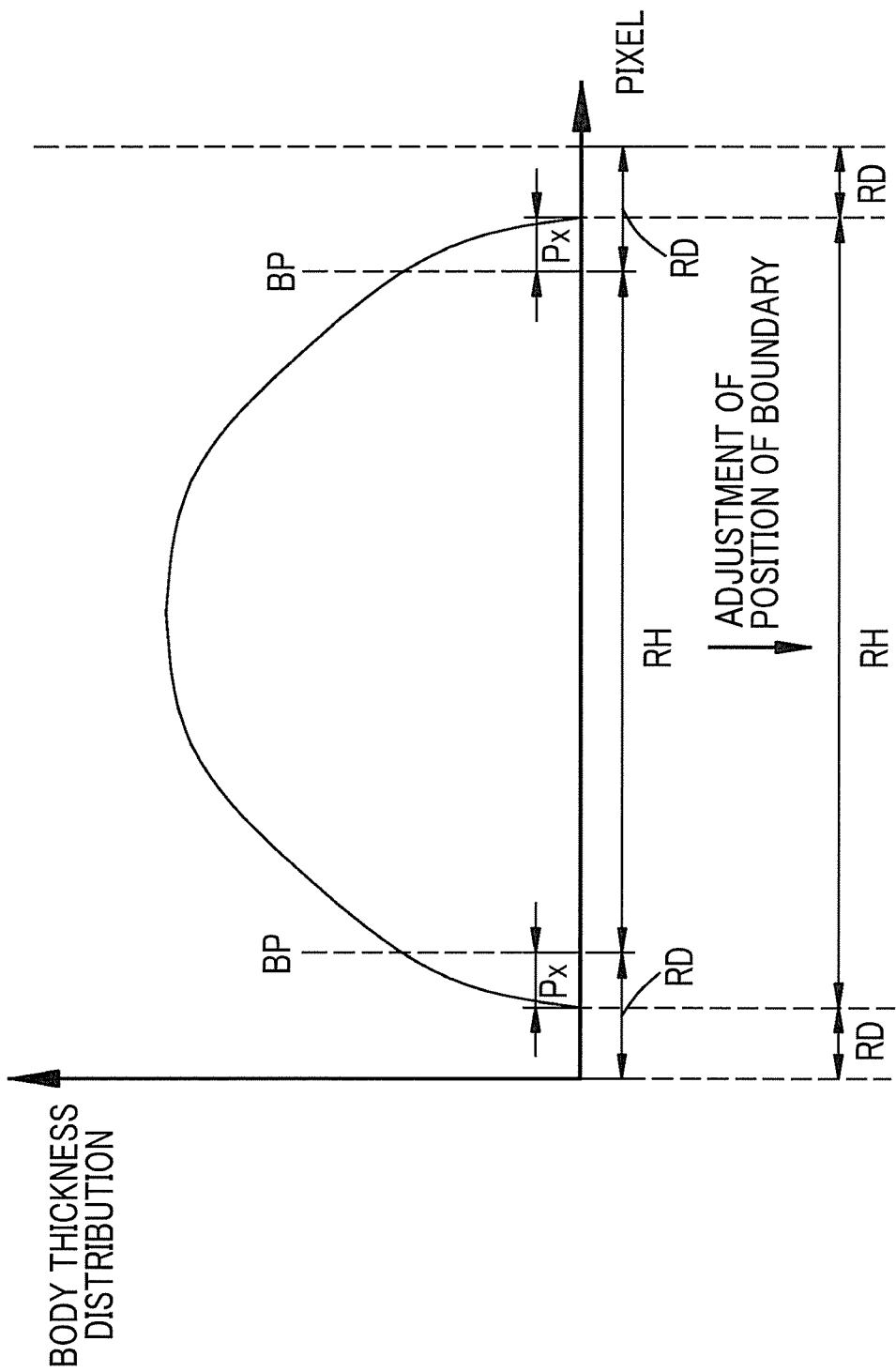
FIG. 7 is a diagram showing the body thickness distribution of a specific line portion.

Specifically, in a case where the specific width is determined from the shape of a subject, that is, the body thickness distribution of a subject among the portions of the subject, a portion Px, of which the body thickness exceeds "0" as shown in the body thickness distribution of a specific line Ls of FIG. 7, of the direct radiation region detected using the threshold value for a region is determined as the specific width. In a case where the position BP of the boundary is adjusted by a specific width corresponding to the portion Px, the subject region is widened by the specific width but the direct radiation region is narrowed by the specific width. Further, in a case where the specific width is determined on the basis of the values of pixels positioned near the position of the boundary, it is preferable that the specific width is determined on the basis of a distance between a pixel that is provided at the position of the boundary and a neighboring pixel that is a pixel positioned in a specific range from the position of the boundary and having a pixel value having a specific range.

Figure 8:
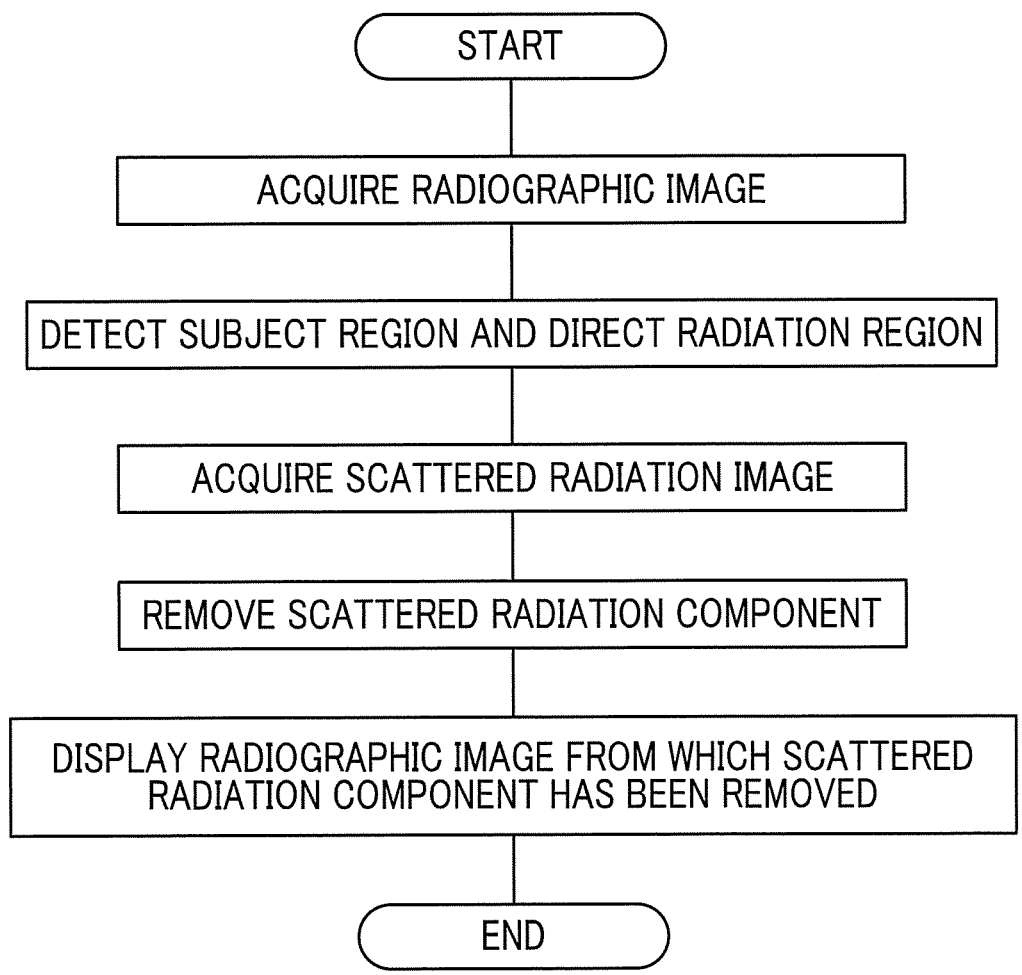
FIG. 8 is a flowchart showing a series of flow of the invention.

Next, processing performed in this embodiment will be described with reference to a flowchart of FIG. 8. The image acquisition unit 31 acquires a radiographic image that is obtained in a case where a subject H irradiated with radiation is imaged by the radiation detection unit including the first and second radiation detectors 15 and 16. It is preferable that the image acquisition unit 31 acquires the first and second radiographic images G1 and G2 having different energy distributions as the radiographic image.

Then, the region detection unit 32 obtains a region detection image by detecting a subject region of the radiographic image where radiation is transmitted through a subject H and reaches the radiation detection unit and a direct radiation region of the radiographic image where radiation directly reaches the radiation detection unit without being transmitted through the subject H. The scattered radiation image-acquisition unit 33 obtains a scattered radiation image about scattered radiation components on the basis of the region detection image and scattered-radiation-spread information about the spread of scattered radiation. The scattered radiation component-removal unit 37 obtains a radiographic image from which scattered radiation components have been removed by subtracting the scattered radiation image from the radiographic image. The radiographic image from which the scattered radiation components have been removed is displayed on the display unit 18.

The first and second radiographic images G1 and G2 are acquired in the embodiment by one-shot energy subtraction, but the first and second radiographic images G1 and G2 may be acquired by a two-shot method that includes causing radiation having different energy distributions to be transmitted through the subject at different timings and detecting the radiation by one radiation detection unit. Any one of an imaging condition at the time of acquisition of the first radiographic image G1 or an imaging condition at the time of acquisition of the second radiographic image G2 may be used in the case of the two-shot method. Further, there is a possibility that the positions of the subject H included in the first and second radiographic images G1 and G2 may be shifted from each other due to motion of the subject H in the case of the two-shot method. For this reason, it is preferable that the positions of subject in the first and second radiographic images G1 and G2 are aligned with each other.

For example, a plurality of first band images and a plurality of second band images representing structures having different frequency bands in the first and second radiographic images G1 and G2 are generated, shift distances between the positions corresponding to each other in the first and second band images of corresponding frequency bands are acquired, and the first and second radiographic images G1 and G2 are aligned with each other on the basis of the shift distances.

EXPLANATION OF REFERENCES

10: imaging device
12: computer
13: radiation source
14: top board
15: first radiation detector
16: second radiation detector
17: radiation energy conversion filter 18: display unit
19: input unit
21: CPU
22: memory
23: storage
30: radiographic image processing device
31: image acquisition unit
32: region detection unit
33: scattered radiation image-acquisition unit
33a: table for scattered-radiation-spread information
34: direct radiation region-pixel value-calculation unit
34a: table for direct radiation region
35: pixel value replacement unit
36: boundary position adjustment unit
37: scattered radiation component-removal unit
RH: subject region
RD: direct radiation region
H: subject
G: radiographic image
Ls: specific line
CP: central portion
BP: position of boundary
Px: specific width

What is claimed is:

1. A radiographic image processing device comprising:
a storage medium; and
a processor coupled to the storage medium and configured to:
acquire a radiographic image obtained in a case where a subject irradiated with radiation is imaged by a radiation detector;
obtain a region detection image by detecting a subject region of the radiographic image in which the radiation is transmitted through the subject and reaches the radiation detector and a direct radiation region of the radiographic image in which the radiation directly reaches the radiation detector without being transmitted through the subject;
obtain a scattered radiation image about a scattered radiation component on a basis of the region detection image and scattered-radiation-spread information about spread of scattered radiation;
obtain a radiographic image from which the scattered radiation component has been removed by subtracting the scattered radiation image from the radiographic image;
obtain an unsaturated scattered radiation pixel value corresponding to a dose of radiation for imaging, which is the dose of the radiation with which the subject is irradiated, with reference to an unsaturated-scattered-radiation-pixel-value relationship representing a relationship between the dose of the radiation and the unsaturated scattered radiation pixel value which is an unsaturated pixel value obtained in consideration of an influence of the scattered radiation without saturation of the pixel value; and
replace a pixel value of the direct radiation region of the scattered radiation image with the unsaturated scattered radiation pixel value, wherein the processor is configured to subtract the scattered radiation image from the radiographic image comprising:
subtract the scattered radiation image, of which the pixel value has been replaced with the unsaturated scattered radiation pixel value, from the radiographic image.

2. The radiographic image processing device according to claim 1,
wherein the processor is further configured to detect a region of the radiographic image in which a pixel value is smaller than a threshold value for a region as the subject region, and detects a region of the radiographic image in which a pixel value is equal to or larger than the threshold value for a region as the direct radiation region.

3. The radiographic image processing device according to claim 1, wherein the unsaturated-scattered-radiation-pixel-value relationship is predetermined for each imaging condition in a table for the direct radiation region, and
the the processor is configured to use any unsaturated-scattered-radiation-pixel-value relationship corresponding to the imaging condition at the time of imaging of the subject or use a combination of a plurality of unsaturated-scattered-radiation-pixel-value relationships satisfying the imaging condition at the time of imaging of the subject, with reference to the table for the direct radiation region.

4. The radiographic image processing device according to claim 1, wherein the processor further configured to:
adjust a position of a boundary between the subject region and the direct radiation region by a specific width,
wherein the processor is configured to obtain the scattered radiation image on a basis of the scattered radiation image in which the position of the boundary has been adjusted and the scattered-radiation-spread information about the spread of the scattered radiation.

5. The radiographic image processing device according to claim 4,
wherein the position of the boundary is adjusted in a case where a pixel value of the direct radiation region exceeds a threshold value for a pixel value or a case where a dose of the radiation exceeds a threshold value for a dose of radiation.

6. The radiographic image processing device according to claim 4,
wherein the specific width is determined on a basis of at least one of a portion of the subject, a method of imaging the subject, a dose of the radiation, or imaging menu information.

7. The radiographic image processing device according to claim 4,
wherein the specific width is determined on a basis of a value of a pixel positioned near the position of the boundary in the radiographic image.

8. The radiographic image processing device according to claim 1, wherein the scattered-radiation-spread information is predetermined for each imaging condition in a table for scattered-radiation-spread information, and
the processor is configured to use any scattered-radiation-spread information corresponding to the imaging condition at the time of imaging of the subject or use a combination of a plurality of pieces of scattered-radiation-spread information satisfying the imaging condition at the time of imaging of the subject, with reference to the table for scattered-radiation-spread information.

9. The radiographic image processing device according to claim 1, wherein the radiation is transmitted through the subject and a top board on which the subject is placed and is incident on the radiation detector, and
the scattered-radiation-spread information is a function of determining two-dimensional spread of the scattered radiation of the radiation incident on any point on the top board.

10. A method of operating a radiographic image processing device, the method comprising:

acquiring a radiographic image obtained in a case where a subject irradiated with radiation is imaged by a radiation detector;

obtaining a region detection image by detecting a subject region of the radiographic image in which the radiation is transmitted through the subject and reaches the radiation detection unit and a direct radiation region of the radiographic image in which the radiation directly reaches the radiation detector detection unit without being transmitted through the subject;

obtaining a scattered radiation image about a scattered radiation component on a basis of the region detection image and scattered-radiation-spread information about spread of scattered radiation;

obtaining a radiographic image from which the scattered radiation component has been removed by subtracting the scattered radiation image from the radiographic image;

obtaining an unsaturated scattered radiation pixel value corresponding to a dose of radiation for imaging, which is the dose of the radiation with which the subject is irradiated, with reference to an unsaturated-scattered-radiation-pixel-value relationship representing a relationship between the dose of the radiation and the unsaturated scattered radiation pixel value which is an unsaturated pixel value obtained in consideration of an influence of the scattered radiation without saturation of the pixel value; and replacing a pixel value of the direct radiation region of the scattered radiation image with the unsaturated scattered radiation pixel value, and wherein subtracting the scattered radiation image from the radiographic image comprising:

subtracting the scattered radiation image, of which the pixel value has been replaced with the unsaturated scattered radiation pixel value, from the radiographic image.

11. A non-transitory computer readable medium for storing a computer-executable program to be loaded into a processor for operating a radiographic image processing device, the computer-executable program causing a computer to perform:

image acquisition processing for causing the processor to acquire a radiographic image obtained in a case where a subject irradiated with radiation is imaged by a radiation detector;

region detection processing for causing the processor to obtain a region detection image by detecting a subject region of the radiographic image in which the radiation is transmitted through the subject and reaches the radiation detector and a direct radiation region of the radiographic image in which the radiation directly reaches the radiation detector without being transmitted through the subject;

scattered radiation image-acquisition processing for causing the processor to obtain a scattered radiation image about a scattered radiation component on a basis of the region detection image and scattered-radiation-spread information about spread of scattered radiation;

scattered radiation component-removal processing for causing the processor to obtain a radiographic image from which the scattered radiation component has been removed by subtracting the scattered radiation image from the radiographic image;

direct radiation region-pixel value-calculation processing for obtaining an unsaturated scattered radiation pixel value corresponding to a dose of radiation for imaging, which is the dose of the radiation with which the subject is irradiated, with reference to an unsaturated-scattered-radiation-pixel-value relationship representing a relationship between the dose of the radiation and the unsaturated scattered radiation pixel value which is an unsaturated pixel value obtained in consideration of an influence of the scattered radiation without saturation of the pixel value; and a pixel value replacement processing for replacing a pixel value of the direct radiation region of the scattered radiation image with the unsaturated scattered radiation pixel value, and wherein subtracting the scattered radiation image from the radiographic image comprising:

subtracting the scattered radiation image, of which the pixel value has been replaced with the unsaturated scattered radiation pixel value, from the radiographic image.

* * * * *